(12) United States Patent
Kress

(10) Patent No.: US 11,232,404 B2
(45) Date of Patent: *Jan. 25, 2022

(54) LINKAGE OF RELATIONSHIP AND TRANSACTION DATA

(71) Applicant: HealthVerity, Inc., Villanova, PA (US)

(72) Inventor: Andrew Kress, Villanova, PA (US)

(73) Assignee: HealthVerity, Inc., Villanova, PA (US)

( * ) Notice: Subject to any disclaimer, the term of this patent is extended or adjusted under 35 U.S.C. 154(b) by 383 days.

This patent is subject to a terminal disclaimer.

(21) Appl. No.: 16/456,461

(22) Filed: Jun. 28, 2019

(65) Prior Publication Data

US 2019/0325391 A1 Oct. 24, 2019

Related U.S. Application Data

(63) Continuation of application No. 14/702,311, filed on May 1, 2015, now Pat. No. 10,380,547.

(60) Provisional application No. 61/987,197, filed on May 1, 2014.

(51) Int. Cl.
| | |
|---|---|
| *G06Q 10/10* | (2012.01) |
| *G06Q 50/00* | (2012.01) |
| *G16H 80/00* | (2018.01) |
| *G16H 40/20* | (2018.01) |
| *G16H 10/60* | (2018.01) |

(52) U.S. Cl.
CPC ............ *G06Q 10/10* (2013.01); *G06Q 50/01* (2013.01); *G16H 40/20* (2018.01); *G16H 80/00* (2018.01); *G16H 10/60* (2018.01)

(58) Field of Classification Search
CPC ..................................................... G06Q 10/10
See application file for complete search history.

(56) References Cited

U.S. PATENT DOCUMENTS

| | | | |
|---|---|---|---|
| 6,397,224 | B1 | 5/2002 | Zubeldia et al. |
| 6,732,113 | B1 | 5/2004 | Ober et al. |
| 2008/0040151 | A1 | 2/2008 | Moore |
| 2010/0070306 | A1 | 3/2010 | Dvorak et al. |
| 2011/0235799 | A1 | 9/2011 | Sovio et al. |
| 2012/0323998 | A1 | 12/2012 | Schoen et al. |
| 2013/0262357 | A1 | 10/2013 | Amarasingham et al. |

OTHER PUBLICATIONS

PTO-892 in parent case U.S. Appl. No. 14/702,311 on Dec. 21, 2017 (Year: 2017).*

(Continued)

*Primary Examiner* — Aryan E Weisenfeld
(74) *Attorney, Agent, or Firm* — Blank Rome LLP

(57) ABSTRACT

A system and method for providing an individual with information on the transaction of other members of that individual's social network while preserving individual anonymity. The method including de-identifying or encrypting individually identifiable relationship data, de-identifying or encrypting individually identifiable transaction data, and linking the de-identified relationship data and the de-identified transaction data. The disclosed system uses the same hash function or encryption algorithm to de-identify or encrypt both the relationship data and the transaction data, enabling the system to identify and link records associated with the same user in both data sets by making a deterministic or probabilistic determination.

20 Claims, 6 Drawing Sheets

(56) References Cited

OTHER PUBLICATIONS

PTO-892 in parent case U.S. Appl. No. 14/702,311 on Jul. 5, 2018 (Year: 2018).*
Durham et al.. "Private Medical Record Linkage with Approximate Matching", AMIA Annual Symposium Proceedings Archive, 2010; 7 pages.
Schnell et al., "Privacy-Preserving Record Linkage using Bloom Filters", BMC Medical Informatics and Decision Making, 2009, vol. 9-41; pp. 1-11.

* cited by examiner

LINKAGE OF RELATIONSHIP AND TRANSACTION DATA

CROSS REFERENCE TO RELATED APPLICATION

This application is a continuation of U.S. patent application Ser. No. 14/702,311, which claims priority to U.S. Prov. Pat. Appl. No. 61/987,197, the disclosure of which is incorporated herein by reference.

BACKGROUND

Field of the Invention

The present invention relates to data to support de s on-making, more specifically data to support healthcare decision-snaking.

Background of the Invention

According to the Pew Internet Life survey, 72 percent of adult internet users say they looked online for health information within the past year. Of these, 77 percent of online health seekers say they began at a search engine such as Google, Bing, or Yahoo. Another 13 percent say they began at a site that specializes in health information, like WebMD. Just 2 percent say they started their research at a more general site like Wikipedia and an additional 1 percent say they started at a social network site like Facebook.

Most online health information-seeking activity to date has focused on disease and treatment, with over half of all users engaging in looking for information relevant to disease and diagnosis. Notably, despite the availability of a number of sites that facilitate provider reviews, health care reviews have not caught on among general consumers. While 8 in 10 internet users say they have researched a product or service online, less than one in five internet users have consulted online reviews and rankings of health care service providers and treatments. Similarly, when it comes to writing reviews of general-interest items, 37 percent of internet users say they have rated a product, service, or person online and 32 percent have posted a comment or review online about product they bought or service they received. People are much less likely to post a review of a treatment, hospital, or clinician. Between 3-4 percent of internet users have done so.

Compared to many other consumer-directed areas, healthcare recommendations, particularly around healthcare provider choice, still remains an area that is dominated by the word-of-mouth opinions of friends and family as well as the recommendation and referral of the patient's current healthcare provider as opposed to utilizing unverified and uncurated healthcare provider reviews online. According to the Center for Studying Health System Change, over 50 percent of primary care choices are aided by word-of-mouth from friends or relatives. While that number drops to approximately 20 percent for specialists, it can be surmised that the reduction is partially due to the increased role of the healthcare provider in recommending referrals to the patient as well as the difficulty of the patient finding relevant information for more specialized needs within a narrow offline friends and family network. Additionally, with the proliferation of health plan options and with the growing need for consumers to select healthcare providers from ever changing lists of in-network and out-of-network providers, the need for consumers to identify new healthcare providers will only continue to increase.

Traditional reasons patients search for new healthcare providers include suspecting a new condition or problem, seeking a second opinion, moving, changing insurance, dissatisfaction with their current doctor, costs, or needing a certain procedure. As noted, today this is usually accomplished by word-of-mouth from family and friends or by recommendation by healthcare providers. While a number of sites such as Healthgrades, Vitals, WebMD, Yelp, Practice Fusion and Zocdoc provide some sort of doctor search functionality, most sites rely on a combination of quasi-factual directory information (provider specialty, payers accepted, education, location, hours) and patient reviews, and none of these sites leverage any sort of trusted referral methodology. Unfortunately, the lack of scale, comprehensiveness, and currency of patient reviews combined with the lack of curation means that most individuals do not use or trust these reviews today. For many other subject areas such as finding a restaurant or buying consumer electronics, the nature of those doing the reviewing may not be highly relevant to those reading the reviews. In healthcare, however, most patients and caregivers have a more complex view of who to trust in determining which healthcare providers to use and the quality of the healthcare providers that is not being met by current models.

According to a 2014 Associated Press-NORC Center for Public Affairs Research study, family and friends are the most trusted source of quality ratings about doctors, with over 60% of Americans saying they would very much or completely trust quality ratings of doctors or other health care providers they receive from friends or family members, versus roughly half saying they would trust quality ratings they receive from their regular doctor or other individual health care provider. Beyond those two sources, however, Americans overwhelmingly lack trust in other sources of quality ratings of health care providers. Current provider ratings websites rank near the bottom, with only 10% saying they trust the quality ratings they receive from these sources.

Therefore, there is a need for an improved system and method of storing, linking, querying, and reporting healthcare data.

SUMMARY

In order to overcome these and other drawbacks of the related art, there is provided a system and method for providing an individual with information on the actual transactions of other members of that individual's social network. The system and method may provide a source of referrals by linking the social graph or social relationships of an individual (e.g., generated through their participation in an online social network) to the transaction data associated with members of that individual's social network (e.g., healthcare providers and the attributes of those healthcare providers that are treating members of that individual's social network). The system and method may allow the individual to see all the healthcare providers that his or her social network already use in a way that protects the identities and healthcare data privacy of the unique individuals in the group. The system and method may also be used to allow an individual to see the experience in his or her social network with other healthcare utilization, for example with particular healthcare facilities, procedures done, and other medical related activities.

BRIEF DESCRIPTION OF THE DRAWINGS

Exemplary embodiments will be set forth with reference to the drawings, in which.

DETAILED DESCRIPTION OF EXEMPLARY EMBODIMENTS

Figure 1:
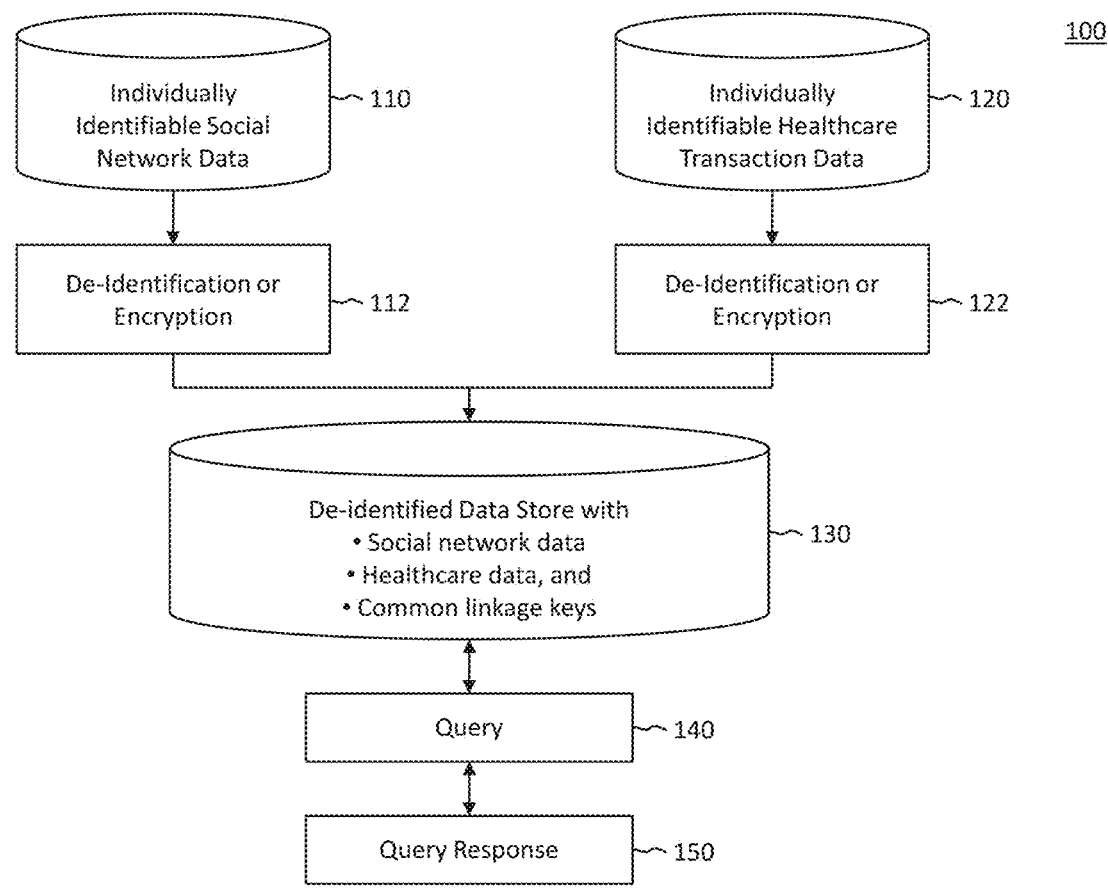
FIG. 1 is a prospective view illustrating a process for data aggregation, de-identification, and linkage according to an exemplary embodiment of the present invention.

Exemplary embodiments of the present invention will be set forth in detail with reference to the accompanying drawings, in which like reference numerals refer to like elements throughout.

Referring now to the invention in more detail, FIG. 1 is a prospective view illustrating a process 100 for data aggregation, de-identification, and linkage according to an exemplary embodiment of the present invention. The process 100 may include a series of components to enable the de-identification, linkage, querying and reporting of social network data linked to healthcare data. Referring to FIG. 1, the process 100 may include a data store 110 containing a source of social network relationship data, a data store 120 containing a source of healthcare transactional data, methods 112 and 122 for de-identifying or encrypting personally identifiable information in each data store, a method for linking data from the two data stores 110 and 120 in a de-identified data store 130, and the ability to query the data 140 regarding data related to a specific individual and receive a response 150.

The social network data 110 includes social network data records that are produced by a social network site and includes individually identifiable data fields such as but not limited to name, date of birth, gender, geographic location or other personally identifiable data that shows the identities of each member of the social network as well as the links or associations between each individual in the social network and all other members of his or her social network that is created by the process of individuals associating with each other online through the social network.

The healthcare transaction data 120 includes individual-level healthcare clinical or transactional data that may be generated from one or more sources of healthcare information such as but not limited to pharmacies, health insurance claims processors or clearinghouses, insurers, or provider organizations, and includes some or all of the same data fields as noted in the prior step above such as but not limited to name, date of birth, gender, geographic location or other personally identifiable data that shows the identities of each individual in the data as well as their associated healthcare transactions that identify the treating physician such as physician office visits or dispensed prescriptions.

There is shown a process 112 for using a hash function or encryption algorithm or other method to de-identify the data records and replace the identifiable data fields noted in the step above for the data records of all of the individuals who are the subject of the social network data and producing a file that contains each unique individual key tied to the unique keys of other individuals in their social network as contained in the social network data store. In a further iteration, this step may also contain a separate individual customer or member identifier generated by the social network data provider. There are a number of published and commercially available methods that permit such de-identification and deterministic or probabilistic linkage to occur. Examples of such de-identification and matching processes are reported in U.S. Pat. Nos. 6,732,113 and 6,397,224, or made available commercially by companies such as Management Science Associates Inc. (http://msa.com/life-sciences/solutions/de-identification-engine) and Universal Patient Key, Inc. (http://universalpatientkey.com/). Further examples exist in the literature, such as Durham E., Xue Y., Kantarcioglu M., and Malin B., Private Medical Record Linkage with Approximate Matching, American Medical Informatics Association 2010 Symposium Proceedings, 182-186; and Schnell R., Bachteler T., and Reiher J., Privacy-preserving record linkage using Bloom filters, BMC Medical Informatics and Decision Making 2009, 9:41.

There is shown the same process 122 as in the prior step for using a the same hash function or encryption algorithm noted in the step above to replace the identifiable data fields above for the data records of all the individuals who are the subject of the healthcare data producing a file that contains a unique individual key for each person that is contained in the healthcare data store tied to each of their healthcare clinical or transactional data.

As the same hash function or encryption algorithm 112 and 122 is used in both of the prior two steps, the unique individual key that is generated by the hash function or algorithm for each individual that is common to both data sets will be the same (or similar enough that the system is able to match common individual keys by deterministic or probabilistic matching). The system links data for each individual in the social network data store and data for the same individual in the healthcare data store. For example, a name and date of birth from the social media data record may generate a key after being hashed or encrypted that may be matched either deterministically or probabilistically to the same name and date of birth being hashed or encrypted in the healthcare data.

There is shown a process for assembling the social network data and the healthcare data for all individuals in both data stores into one or more related data stores 130 that may be linked at the individual level by the unique key generated in the prior three steps. As noted, there are a number of alternate methods for linking on various series of information that rely on both the exact matching of the keys (deterministic) or matching of the keys based on degrees of similarity (probabilistic).

Figure 2:
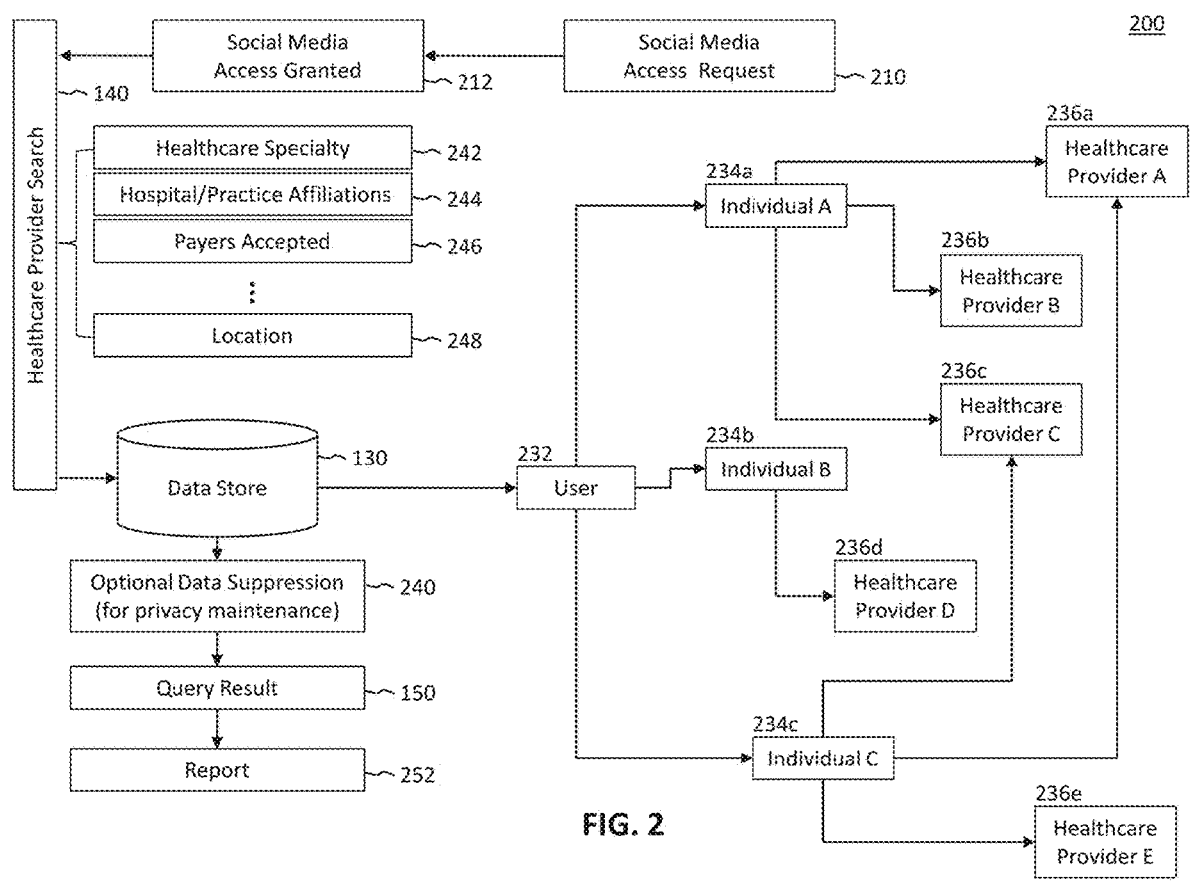
FIG. 2 is a prospective view illustrating a process for generating a resulting physician dataset according to an exemplary embodiment of the present invention.

FIG. 2 is a prospective view illustrating a process 200 for generating a dataset of healthcare providers according to an exemplary embodiment of the present invention.

The process 200 may include a process 210 for an individual accessing a website or mobile application using their social network login or other information to identify them and associate them with their social network data.

A user may be granted access to the social media profile and the user may be associated with other users in one or more social networks in process 212.

As seen in FIG. 2, there is shown a process for the user submitting the query 140 via the website or mobile application against the data store 130 assembled in the prior steps in order to provide a combined series of records of all healthcare services utilization for their user-defined social network. As one mechanism of increasing the specificity of the query 140, the query 140 can be limited by the user based on selected criteria 240 about the healthcare providers that provided the healthcare services in the data, such as (but not limited to) the medical specialty 242 of a treating physician or other healthcare provider, the hospital, practice group or other professional affiliations 244 of a physician or other healthcare provider, the payers 246 that the healthcare provider accepts, and the geographic location 248 of the healthcare provider. That query would be run against the combined data store 130 that includes the social network linkages as well as the healthcare data, and would provide an assembled dataset in response to the aforementioned query 140 that uses a set of unique keys from specific individuals generated from the social network data tied to the user and who relate to each other via the connections within the social network data. Such keys may be linked to the actual associated healthcare data for those individuals, such as physician office visits, and from the healthcare data would include treating physician names or identifiers or other healthcare related information such as procedures performed or diagnoses for each healthcare service in the data store for each of these keys.

In the example shown in FIG. 2, the user performing the query 140 is assigned an individual user ID 252. The user's social network(s) includes linked individuals 234a, 234b, and 234c. The de-identified data store 130 indicates that individual 234a is linked to healthcare providers 236a, 236b, and 236c and individual 234b is linked to healthcare provider 236d. The de-identified data store 130 also indicates that individual 364c is linked to healthcare provider 236a and 236b, respectively). Finally, individual 234c is linked to healthcare provider 236e.

The process 200 may also include a process 150 for summarizing the data to report on the combined listing of the data produced in the prior step. Such summarization may include but not be limited to rank order by frequency of occurrence or other measures.

The process 200 may also include an optional step 240 to suppress any query results that have frequency or other descriptive characteristics that may create a risk of the underlying source healthcare data being re-identified by the user as to the actual identities of the individuals who received such services.

The process 200 may also include a process 252 for displaying the combined data produced in the prior step either through a web browser or mobile or desktop computer application so that a individual can see a listing of all healthcare providers that have treated other individuals who are linked to that individual through their social network, without seeing the specific identities of the linked individuals that associate to each healthcare provider, as the linkage has been made without the need to expose identifiable data.

This process 200 can also be applied to other healthcare utilization data generated from the healthcare data sources above besides healthcare provider names, in order to allow an individual user to see the compilation of other healthcare usage of the individual's social network, such as hospital names, procedures performed, or drugs used.

The advantages of the present invention include, without limitation, the ability to leverage an individual's social network to link to existing large-scale healthcare datasets in a privacy-protecting fashion as well as the ability to do this on a broad scale, unlike other online reviews which are based on user-generated reviews from users not related to the individual seeking recommendations, and as such are not as trustworthy and require significant time to produce any adequate volume of reviews about a specific healthcare provider.

Figure 3:
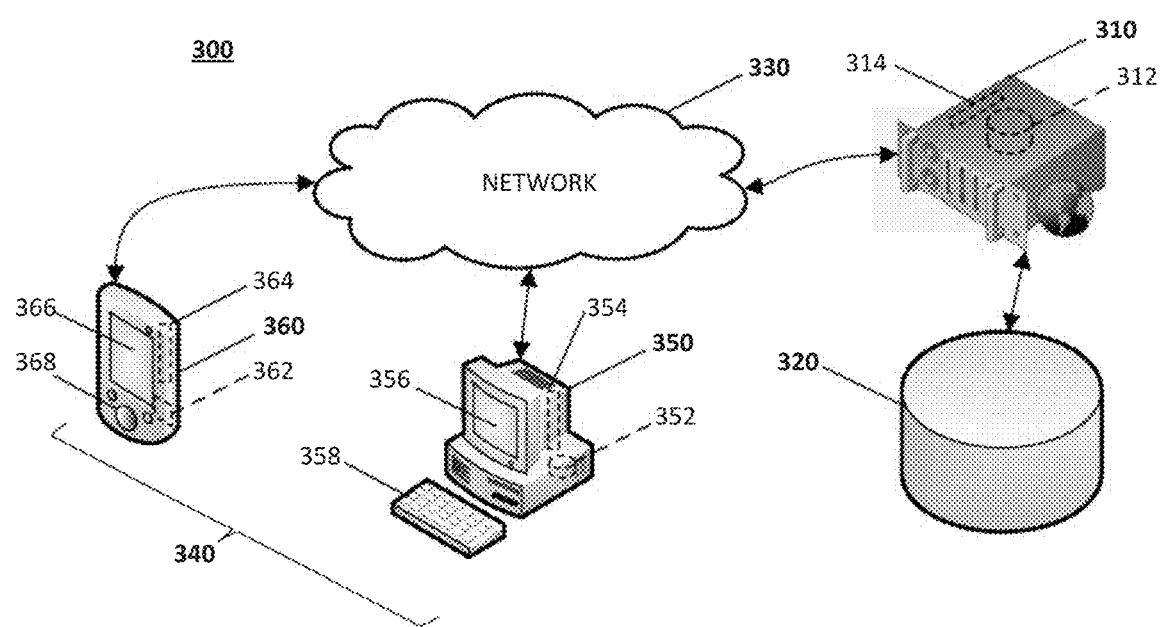
FIG. 3 is an overview of a system according to an exemplary embodiment of the present invention.

FIG. 3 is an overview of the system 300 according to an exemplary embodiment of the present invention.

The system 300 may include one or more servers 310 and one or more databases 320 connected to a plurality of remote computer systems 340, such as one or more personal systems 350 and one or more mobile computer systems 360, via a network 330.

The one or more servers 310 may include an internal storage device 312 and a processor 314. The one or more servers 310 may be any suitable computing device including, for example, an application server and a web server which hosts websites accessible by the remote computer systems 340. The one or more databases 320 may be internal to the server 310, in which case they may be stored on the internal storage device 312, or it may be external to the server 312, in which case it may be stored on an external non-transitory computer-readable storage medium, such as an external hard disk array or solid-state memory. The one or more databases 320 may be stored on a single device or multiple devices. The network 330 may include any combination of the internet, cellular networks, wide area networks (WAN), local area networks (LAN), etc. Communication via the network 330 may be realized by wired and/or wireless connections. A remote computer system 340 may be any suitable electronic device configured to send and/or receive data via the network 330. A remote computer system 340 may be, for example, a network-connected computing device such as a personal computer, a notebook computer, a smartphone, a personal digital assistant (PDA), a tablet, a notebook computer, a portable weather detector, a global positioning satellite (GPS) receiver, network-connected vehicle, etc. The one or more personal computer systems 350 may include an internal storage device 352, a processor 354, output devices 356 and input devices 358. The one or more mobile computer systems 360 may include an internal storage device 362, a processor 364, output devices 366 and input devices 368. The internal storage devices 312, 352, and/or 362 may be non-transitory computer-readable storage mediums, such as hard disks or solid-state memory, for storing software instructions that, when executed by a processor 314, 354, or 364, carry out relevant portions of the features described herein. The processors 314, 354, and/or 364 may include a central processing unit (CPU), a graphics processing unit (GPU), etc. The processors 314, 354, and 364 may be realized as a single semiconductor chip or more than one chip. An output device 356 and/or 366 may include a display, speakers, external ports, etc. A display may be any suitable device configured to output visible light, such as a liquid crystal display (LCD), a light emitting polymer display (LPD), a light emitting diode (LED), an organic light emitting diode (OLED), etc. The input devices 358 and/or 368 may include keyboards, mice, trackballs, still or video cameras, touchpads, etc. A touchpad may be overlaid or integrated with a display to form a touch-sensitive display or touchscreen.

The system 300 may be used by a single user or multiple users simultaneously. The system 300 may be realized by software instructions accessible to and executed by the server 310 and/or downloaded and executed by the remote computing system 340. As used herein, the term "users" may refer to individuals, organizations, or entities.

The social network data 110, healthcare transaction data 120, and de-identified data 130 may be stored in one or more non-transitory computer readable storage mediums (for example, the database(s) 320). Each data store 110, 120, and 130 may include one or more databases. Alternatively, the data stores 110, 120, and/or 130 may be stored in the same database. Each of the process steps (for example, the process 100, the process 200, etc.) may be stored in a non-transitory computer readable storage medium for execution by one or more processors.

Figure 4A:
FIG. 4A illustrates a graphical user interface according to an exemplary embodiment of the present invention.

FIG. 4A illustrates a graphical user interface output to a remote computer system 340 according to an exemplary embodiment of the present invention.

A user may request access to one or more social networks as described in step 210 above. In the example shown, the user may separately request access social networks, such as FACEBOOK, GOOGLE PLUS, and LINKED IN. Alternatively, the user interface may enable a user to request access to multiple social media accounts with a single login. The login may be provided by one of the social media services or a third party service. The user interface may include an optional feature 412 that enables a user to search healthcare providers associated with the user's social network(s) (e.g., the user's friends or direct connections) or associated with the user's extended social network(s) (e.g., friends of the user's friends or individuals that are connected to the user my more than one degree).

As described above, the user may perform a query 140 (or filter query results 150) by specifying a location 248. The query 140 may include a geographic location (e.g., a municipality or other geographic area). Alternatively, the query may include all locations within a radius of a geographic location or within a radius of the location of the remote computer 340. The location of the remote computer 340 may be determined by GPS, cellular network triangulation, IP address, etc. In the example shown in FIG. 4A, the query 140 includes all medical practices and hospitals within 5 miles of the 19146 zip code.

In the embodiment shown in FIG. 4A, the query results 150 are output to map view 400a. The query results 150 may include, for example, information regarding each healthcare provider (e.g., the type of healthcare provider) and/or the popularity of the healthcare provider within the user's social network(s) or extended social network(s) (e.g., the number of contacts within the user's social network(s) or extended social network(s) with healthcare records that indicate an association with each healthcare provider).

Figure 4B:
FIG. 4B illustrates a graphical user interface according to another exemplary embodiment of the present invention.

FIG. 4B illustrates a graphical user interface output to a remote computer system 340 according to another exemplary embodiment of the present invention. The user may request access to one or more social networks as described in step 210 above. The user may perform a query 140 (or filter query results 150) by specifying a location 248. The user may also specify the type of healthcare provider, healthcare provider specialty, payers accepted (e.g., insurance networks), physician gender, physician board certification(s), language(s), hospital or practice affiliation, diseases treated, procedures performed, etc. In the example shown in FIG. 4B, the query 140 includes all primary care physicians 5 miles of the remote computer 340 location.

Figure 5:
FIG. 5 illustrates a graphical user interface according to another exemplary embodiment of the present invention.

FIG. 5 illustrates a graphical user interface output to a remote computer system 340 according to another exemplary embodiment of the present invention.

A user may request access to one or more social networks as described in step 210 above. As described above, the user may perform a query 140 and specify a location 248. In the example shown in FIG. 5, the query results 150 are shown in a list view, which may be sorted by popularity within the user's social network(s), name, address (e.g. distance from location 248), rating, etc. The popularity within the user's social network(s) may be determined based on the number of individuals in the user's social network(s) (e.g., friends) with healthcare records that indicate use of the healthcare provider, the number of individuals in the user's extended social network(s) (e.g., friends of friends) that have used the healthcare provider, the number of visits to the healthcare provider from individuals in the user's social network(s) or extended social network(s), etc. The system 300 may also allow users to rate healthcare providers. The ratings may be de-identified or encrypted as described above to enable a user to provide an anonymous rating to individuals within his or her social network(s).

As used herein, the term "healthcare provider" may include doctors, medical professionals, hospitals, medical practices, diagnostic centers, imaging centers, medical suppliers, medical services, urgent care clinics, retail clinics, pharmacies, etc. As used herein the term "social network" may include any computer platform that indicates relationships between individuals, such as people who share interests, activities, backgrounds, and/or real-life connections.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. A method, comprising:

receiving individually identifiable relationship data associated with a first user and a second user, the individually identifiable relationship data associated with the second user including a link or association with the first user;

receiving individually identifiable transaction data associated with the first user;

de-identifying or encrypting the individually identifiable relationship data associated with the first user to form de-identified relationship data associated with the first user by using a hash function or encryption algorithm to generate a first key and replacing data identifying the first user with the first key;

de-identifying or encrypting the individually identifiable transaction data associated with the first user to form de-identified transaction data associated with the first user by using the hash function or encryption algorithm to generate a second key and replacing data identifying the first user with the second key;

identifying de-identified relationship data associated with the first user and de-identified transaction data associated with the first user by making a determination that the first key is identical or similar to the second key;

linking the de-identified relationship data associated with the first user and the de-identified transaction data associated with the first user;

de-identifying or encrypting the individually identifiable relationship data associated with the second user to form de-identified relationship data associated with the second user; and outputting the de-identified transaction data associated with the first user to the second user in response to a determination that the de-identified relationship data associated with the second user includes a link or association with the first user.

2. The method of claim 1, wherein the data identifying the first user includes a name or date of birth of the first user.

3. The method of claim 1, wherein the de-identified transaction data associated with the first user is output to the second user in response to a query initiated by the second user.

4. The method of claim 1, wherein:
the hash function or encryption algorithm generates the first key by hashing or encrypting the data identifying the first user in the individually identifiable relationship data associated with the first user;
the hash function or encryption algorithm generates the second key by hashing or encrypting the data identifying the first user in the individually identifiable transaction data associated with the first user.

5. The method of claim 1, wherein the determination that the first key is identical or similar to the second key is a deterministic or probabilistic determination.

6. The method of claim 1, wherein the individually identifiable relationship data associated with the first user comprises individually identifiable social network data associated with the first user.

7. The method of claim 1, wherein the individually identifiable transaction data associated with the first user comprises individually identifiable healthcare transaction data associated with the first user or individually identifiable clinical data associated with the first user.

8. The method of claim 1, wherein the de-identified transaction data output to the second user identifies a physician of the first user.

9. The method of claim 1, wherein the de-identified transaction data output to the second user identifies a healthcare facility utilized by the first user, a treatment received by the first user, or a medication distributed to the first user.

10. The method of claim 1, wherein receiving individually identifiable relationship data associated with the second user includes a link or association with a third user, the method further comprising:
receiving individually identifiable transaction data associated with the third user;
de-identifying or encrypting the individually identifiable transaction data associated with the third user;
summarizing the de-identified transaction data associated with the first user and the de-identified transaction data associated with the third user; and
outputting, to the second user, the summary of the de-identified transaction data associated with the first user and the de-identified transaction data associated with the third user.

11. A system, comprising:
a relationship database for storing:
individually identifiable relationship data associated with a first user; and
individually identifiable relationship data associated with a second user that includes a link or association with the first user;
a transaction database for storing individually identifiable transaction data associated with the first user; and
a processor configured to:
de-identify or encrypt the individually identifiable relationship data associated with the first user to form de-identified relationship data associated with the first user by using a hash function or encryption algorithm to generate a first key and replacing the data identifying the first user with the first key;
de-identify or encrypt the individually identifiable transaction data associated with the first user to form de-identified transaction data associated with the first user by using the hash function or encryption algorithm to generate a second key and replacing the data identifying the first user with the second key;
identify de-identified relationship data associated with the first user and de-identified transaction data associated with the first user by making a determination that the first key is identical or similar to the second key;
link the de-identified social network data associated with the first user and the de-identified transaction data associated with the first user;
de-identifying or encrypting the individually identifiable relationship data associated with the second user to form de-identified relationship data associated with the second user; and
output the de-identified transaction data associated with the first user to the second user in response to a determination that de-identified relationship data associated with the second user includes a link or association with the first user.

12. The system of claim 11, wherein the data identifying the first user includes a name or date of birth of the first user.

13. The system of claim 11, wherein the processor outputs the de-identified transaction data associated with the first user to the second user in response to a query initiated by the second user.

14. The system of claim 11, wherein:
the hash function or encryption algorithm generates the first key by hashing or encrypting the data identifying the first user in the individually identifiable relationship data associated with the first user;
the hash function or encryption algorithm generates the second key by hashing or encrypting the data identifying the first user in the individually identifiable transaction data associated with the first user.

15. The system of claim 11, wherein the processor determines that the first key is identical or similar to the second key by making a deterministic or probabilistic determination.

16. The system of claim 11, wherein the individually identifiable relationship data associated with the first user comprises individually identifiable social network data associated with the first user.

17. The system of claim 11, wherein the individually identifiable transaction data associated with the first user comprises individually identifiable healthcare transaction data associated with the first user or individually identifiable clinical data associated with the first user.

18. The system of claim 11, wherein the de-identified transaction data output to the second user identifies a physician of the first user.

19. The system of claim 11, wherein the de-identified transaction data output to the second user identifies a healthcare facility utilized by the first user, a treatment received by the first user, or a medication distributed to the first user.

20. The system of claim 11, wherein:
the individually identifiable relationship data associated with the second user includes a link or association with a third user;
the transaction database stores individually identifiable transaction data associated with the third user; and the processor is configured to:
- de-identify or encrypt the individually identifiable transaction data associated with the third user;
- summarize the de-identified transaction data associated with the first user and the de-identified transaction data associated with the third user; and
- output, to the second user, the summary of the de-identified transaction data associated with the first user and the de-identified transaction data associated with the third user.

* * * * *